United States Patent [19]

Uematsu et al.

[11] 4,404,019
[45] Sep. 13, 1983

[54] 3-CHLORO-1-PHENYL-1,2,4-TRIAZOLIN-5-ONES AND THEIR USE AS HERBICIDES

[75] Inventors: Tamon Uematsu, Funabashi; Shunichi Hashimoto; Hiroshi Matsumoto, both of Sonehigashi, all of Japan

[73] Assignee: Sumitomo Chemical Company, Limited, Osaka, Japan

[21] Appl. No.: 328,719

[22] Filed: Dec. 8, 1981

[30] Foreign Application Priority Data

Dec. 24, 1980 [JP] Japan .................. 55-184515
Dec. 24, 1980 [JP] Japan .................. 55-184516

[51] Int. Cl.³ .................. A01N 43/64; C07D 249/12
[52] U.S. Cl. .................. 71/92; 548/263; 548/264; 548/265; 560/29; 560/30; 564/151; 564/310
[58] Field of Search .................. 548/263, 264, 265; 71/92

[56] References Cited

U.S. PATENT DOCUMENTS 3,867,396  2/1975  Dawes et al. .................. 548/265
4,318,731  3/1982  Kajioka et al. .................. 548/263

FOREIGN PATENT DOCUMENTS 1200825  9/1965  Fed. Rep. of Germany ...... 548/264

OTHER PUBLICATIONS

Pesson et al., Chemical Abstracts, vol. 57, cols. 808–809, (1962).
Kröger et al., Chem. Ber. 102, 755–766, (1969).

*Primary Examiner*—Alton D. Rollins
*Attorney, Agent, or Firm*—Birch, Stewart, Kolasch & Birch

[57] ABSTRACT

A compound of the formula:

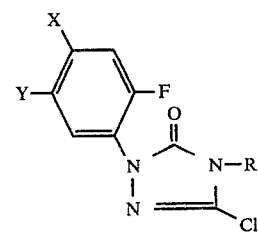

wherein R is a $C_1$–$C_4$ alkyl group, a $C_3$–$C_4$ alkenyl group or a $C_3$–$C_4$ cycloalkyl group, X is a chlorine atom or a bromine atom and Y is a hydrogen atom or a $C_1$–$C_4$ alkoxy group, which is useful as a herbicide.

8 Claims, No Drawings

3-CHLORO-1-PHENYL-1,2,4-TRIAZOLIN-5-ONES AND THEIR USE AS HERBICIDES

The present invention relates to triazolinones, and their production and use. More particularly, it relates to 3-chloro-1-phenyl-1,2,4-triazolin-5-one derivatives, and their production process and herbicidal use.

The said 3-chloro-1-phenyl-1,2,4-triazolin-5-one derivatives (hereinafter referred to as "triazolinone(s)") are representable by the formula:

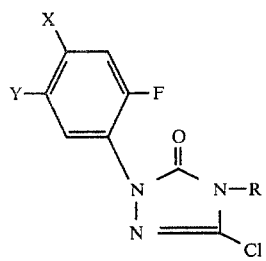

wherein R is a $C_1$-$C_4$ alkyl group, a $C_3$-$C_4$ alkenyl group or a $C_3$-$C_4$ cycloalkyl group, X is a chlorine atom or a bromine atom and Y is a hydrogen atom or a $C_1$-$C_4$ alkoxy group.

Preferred are the triazolinones (I) wherein R is a $C_1$-$C_4$ alkyl group, a cyclopropyl group or an allyl group and Y is a hydrogen atom or a $C_1$-$C_3$ alkoxy group.

In one aspect of the present invention, there is provided the triazolinones (I). In another aspect of this invention, there is provided a herbicidal composition comprising at least one of the triazolinones (I) as an active ingredient. In a further aspect of the invention, there is provided a process for preparing the triazolinones (I) which comprises reacting the corresponding 1-phenyl-1,2,4-triazolidine-3,5-dione derivatives (hereinafter referred to as "triazolidinedione(s)") of the formula:

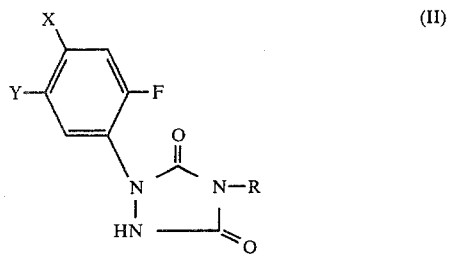

wherein R, X and Y are each as defined above with phosphorus oxychloride.

Some 3-chloro-1,2,4-triazolin-5-one derivatives similar to the triazolinones (I) in chemical structure are known (Kröger et al.: Chem. Ber., 102, 755-766 (1969)). However, their biological activity has never been reported.

As a result of an extensive study, it has now been found that the triazolinones (I) of the invention show a broad herbicidal spectrum against a wide variety of weeds in a crop field. Examples of weeds against which the triazolinones (I) can exert a herbicidal activity are annual and perennial narrow-leaved weeds such as barnyardgrass (*Echinocloa crus-galli*), large crabgrass (*Digitaria sanguinalis*), green foxtail (*Setaria viridis*), Johnsongrass (*Sorghum halepense*), annual bluegrass (*Poa annua*), water foxtail (*Alopecurus geniculata*), quackgrass (*Agropyron repens*), yellow nutsedge (*Cyperus esculentus*), purple nutsedge (*Cyperus rotundus*), flat-sedge (*Cyperus microiria*) and wild oat (*Avena fatua*) and annual and perennial broad-leaved weeds such as tall morningglory (*Iponoea purpurea*), cocklebur (*Xanthium pensylvanicum*), velvetleaf (*Abtilon theophrasti*), prickly sida (*Sida spinosa*), jimsonweed (*Datura stramonium*), sicklepod (*Cassia obtusifolia*), sesbania (*Sesbania spp.*), common ragweed (*Ambrosia artemisifolia*), black nightshade (*Solanum nigrum*), smartweed (*Polygonum spp.*), redroot pigweed (*Amaranthus retroflexus*), common lambsquarters (*Chenopodium album*), common chickweed (*Stellaria media*), common purslane (*Portulaca oleracea*), catchweed bedstraw (*Galium aparine*), bindweed (*Calystegia japonica*), woolypod milkweed (*Asclepias eriocarpa*) and wild mustard (*Brassica arvensis*), etc.

It is notable that, when applied to the crop field, the triazolinones (I) exhibit a significant herbicidal activity in any of the treatment modes such as preemergence soil treatment or post-emergence foliar treatment without causing any injury on the important crop plants (e.g. cotton, soybean, wheat, corn). Further, they may be applied to the paddy field so as to exterminate annual or perennial weeds such as barnyardgrass (*Echinochloa crusgalli*), monochoria (*Monochoria viaginalis*), toothcup (*Rotala indica*), false pimpernel (*Lindernia procumbens*), waterstarwort (*Callitriche verna*), nutsedge sp. (*Cyperus difformis*), slender spikerush (*Eleocharis acicularis*), bulrush (*Scirpus juncoides*), arrowhead (*Sagittaria pygmaea*) and water nutgrass (*Cyperus serotinus*), etc.

Besides, due to their high herbicidal potency and broad herbicidal spectrum, they may be added as herbicides for a vegetable garden, orchard, lawn, pasture, tea garden, mulberry field, rubber plantation, forest, non-agricultural field, etc.

For production of the triazolinone (I), the corresponding triazolidinedione (II) may be reacted with at least an equimolar amount (preferably at a larger excess) of phosphorus oxychloride at an elevated temperature (preferably while refluxing) for a sufficient period of time (preferably from 40 to 50 hours). The presence of a high boiling point solvent such as xylene or toluene in the reaction system is favorable for carrying out the reaction at a higher temperature within a shorter period of time. Recovery of the reaction product from the reaction mixture may be effected by a per se conventional separation procedure. For instance, the reaction mixture is concentrated by distillation under reduced pressure to eliminate excessive phosphorus oxychloride. The resulting oil is admixed with an aqueous alkali such as aqueous sodium hydroxide solution or aqueous potassium hydroxide solution and extracted with a suitable organic solvent. The extract is washed with water, dried over an appropriate drying agent such as anhydrous sodium sulfate or anhydrous magnesium sulfate, filtered and concentrated to give the objective triazolinone (I). For purification, any conventional procedure such as recrystallization or column chromatography may be applied thereto.

The starting triazolidinedione (II) is obtainable by treatment of the semicarbazide carboxylic ester of the formula:

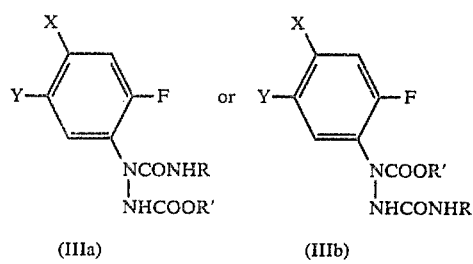

(IIIa)　　　(IIIb)

wherein R' is a $C_1$–$C_4$ alkyl group, and R, X and Y are each as defined above with a base. For instance, the semicarbazide carboxylic ester (IIIa) or (IIIb) may be treated with an equimolar to greatly excessive amount of a base (e.g. sodium hydroxide, potassium hydroxide) in an aqueous medium. In case of the base being used in a greatly excessive amount, the reaction is normally accomplished at a temperature of 80° to 100° C. within 1 to 5 hours. The reaction can proceed even at room temperature, but a higher temperature of 80° to 100° C. is preferred for completion of the reaction within a shorter period of time. When the reaction medium consists of water alone, the reaction system becomes heterogeneous. The use of any water-miscible organic solvent (e.g. methanol, ethanol, tetrahydrofuran, dioxane) in combination with water is thus favorable for making the reaction system homogeneous. Recovery of the produced triazolidinedione (II) from the reaction mixture may be effected by a per se conventional procedure. For instance, the reaction mixture is acidified with an acid such as hydrochloric acid or sulfuric acid. The precipitated crystals are collected by filtration, washed with water and dried. When an oil is separated instead of the crystals, it may be extracted with an organic solvent. The extract is then dried and concentrated. Any conventional purification procedure such as recrystallization or column chromatography may be applied to the thus obtained crude product.

The said semicarbazide carboxylic ester (IIIa) or (IIIb) may be produced by the corresponding 2-fluoro-4-X-5-Y-phenylhydrazine (cf. Japanese Patent Publication (unexamined) No. 89670/1977; U.S. Pat. Nos. 4,124,374, 4,123,252, 4,111,681 and 668,566) according to the following scheme:

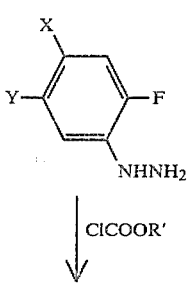

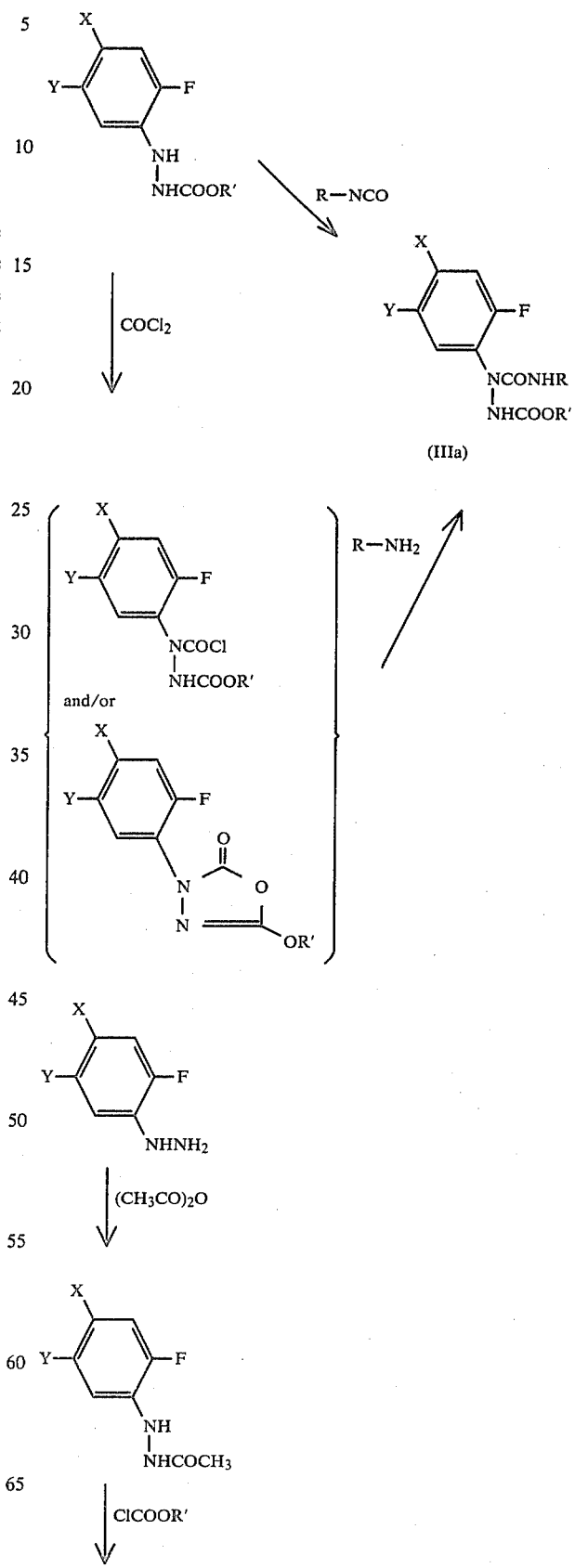

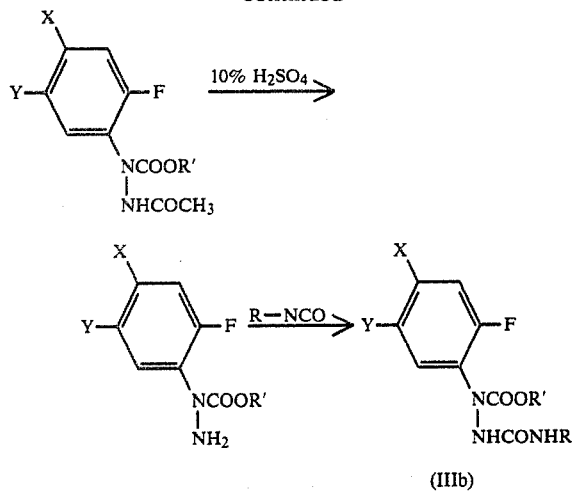

wherein R and R' are each as defined above.

Some practical embodiments of the process for production of the triazolinone (I) of the triazolidinedione (II) are illustratively shown below.

EXAMPLE 1

Production of Compound No. D:

To a solution of 1-(4-chloro-2-fluorophenyl)-1-ethoxycarbonyl-3-isopropylsemicarbazide (58.78 g) in ethanol (200 ml) was added a 5% aqueous solution of sodium hydroxide (500 ml), and the resultant mixture was boiled for 4 hours while stirring. After cooling, the mixture was made acidic with hydrochloric acid. The separated oily substance was extracted with chloroform (100 ml) three times. The chloroform layer was washed with a saturated sodium chloride solution, dried over anhydrous magnesium sulfate and filtered. Removal of chloroform by distillation under reduced pressure gave 47.5 g of 1-(4-chloro-2-fluorophenyl)-4-isopropyl-1,2,4-triazoline-3,5-dione, which crystallized within a few days. Recrystallization of this substance from a mixture of benzene and hexane gave 45.3 g of the objective compound.

M.P., 96°–97° C.

Elementary analysis: Calcd. for C, 48.62%; H, 4.09%; N, 15.47%, Cl, 13.05%. Found: C, 48.47%; H, 4.13%; N, 15.55%; Cl, 13.02%.

EXAMPLE 2

Production of Compound No. E:

To a solution of 2-(4-chloro-2-fluorophenyl)-1-ethoxycarbonyl-4-cyclopropylsemicarbazide (8.4 g) in ethanol (50 ml) was added a 5% aqueous solution of sodium hydroxide (100 ml), and the resultant mixture was boiled for 3 hours while stirring. After cooling, water (100 ml) was added thereto. The mixture was made acidic with hydrochloric acid. The precipitated crystals were filtered, washed with water and dried to obtain 4.8 g of 1-(4-chloro-2-fluorophenyl)-4-cyclopropyl-1,2,4-triazoline-3,5-dione.

M.P., 118°–119° C.

Elementary analysis: Calcd. for $C_{11}H_9N_3O_2ClF$: C, 48.99%; H, 3.37%; N, 15.59%; Cl, 13.15%. Found: C, 49.16%; H, 3.29%; N, 15.68%; Cl, 13.31%.

EXAMPLE 3

Production of Compound No. 4:

4-Isopropyl-1-(4-chloro-2-fluorophenyl)-1,2,4-triazolidine-3,5-dione (6.32 g; 0.023 mol) and phosphorus oxychloride (50 ml) were boiled with stirring for 30 hours. After completion of the reaction, excessive phosphorus oxychloride was removed by distillation under reduced pressure. The separated oily substance was poured into icewater and extracted with chloroform (50 ml) three times. The chloroform layer was washed with a saturated sodium chloride solution until the washings became neutral, dried over anhydrous magnesium sulfate, filtered and concentrated under reduced pressure. The resulting oily substance was chromatographed on silica gel to give 2.5 g of 3-chloro-4-isopropyl-1-(4-chloro-2-fluorophenyl)-1,2,4-triazolin-5-one.

M.P., 73°–74° C.

Elementary analysis: Calcd. for $C_{11}H_{10}N_3OCL_2F$: C, 45.53%; H, 3.48%; N, 14.49%; Cl, 24.44%. Found: C, 45.71%; H, 3.24%; N, 14.30%; Cl, 24.72%.

Some typical examples of the triazolinone (I) and the triazolidinedione (II) prepared in the same manner as above are shown in Tables 1 and 2.

TABLE 1

| Compound No. | X | Y | R | Physical property |
|---|---|---|---|---|
| 1 | Cl | H | $CH_3-$ | M.P. 96–98° C. |
| 2 | Cl | H | $CH_3CH_2-$ | $n_D^{25.7}$ 1.5622 |
| 3 | Cl | H | $CH_3CH_2CH_2-$ | $n_D^{23.8}$ 1.5534 |
| 4 | Cl | H | $(CH_3)_2CH-$ | M.P. 73–74° C. |
| 5 | Cl | H | cyclopropyl ($-CH(CH_2)_2$) | M.P. 76–77° C. |
| 6 | Cl | H | $CH_2=CH-CH_2-$ | $n_D^{23.8}$ 1.5665 |
| 7 | Cl | H | $CH_3CH_2CH_2CH_2-$ | $n_D^{23.8}$ 1.5409 |
| 8 | Cl | H | $CH_3CH_2(CH_3)CH-$ | $n_D^{23.8}$ 1.5476 |
| 9 | Cl | $CH_3O-$ | $(CH_3)_2CH-$ | $n_D^{24.5}$ 1.5574 |
| 10 | Cl | $(CH_3)_2CHO-$ | cyclopropyl ($-CH(CH_2)_2$) | $n_D^{23.5}$ 1.5484 |

TABLE 1-continued

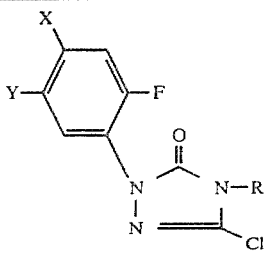

| Compound No. | X | Y | R | Physical property |
|---|---|---|---|---|
| 11 | Br | H | CH2\CH–/CH2 (cyclopropyl) | M.P. 79.5–82° C. |

TABLE 2

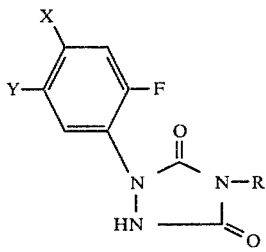

| Compound No. | X | Y | R | Physical property |
|---|---|---|---|---|
| A | Cl | H | CH3— | M.P. 273–274° C. |
| B | Cl | H | CH3CH2— | M.P. 110–113° C. |
| C | Cl | H | CH3CH2CH2— | $n_D^{25.5}$ 1.5428 |
| D | Cl | H | (CH3)2CH— | M.P. 96–97° C. |
| E | Cl | H | CH2\CH–/CH2 (cyclopropyl) | M.P. 118–119° C. |
| F | Cl | H | CH2=CH—CH2— | $n_D^{25.5}$ 1.5268 |
| G | Cl | H | CH3CH2CH2CH2— | $n_D^{23.0}$ 1.5100 |
| H | Cl | H | CH3CH2\CH–/CH3 | $n_D^{25.5}$ 1.5278 |
| I | Cl | CH3O— | CH3CH—/CH3 | M.P. 158–161.8° C. |
| J | Cl | (CH3)2CHO— | CH2\CH–/CH2 (cyclopropyl) | $n_D^{25.5}$ 1.5279 |

TABLE 2-continued

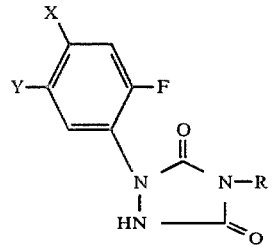

| Compound No. | X | Y | R | Physical property |
|---|---|---|---|---|
| K | Br | H | CH2\CH–/CH2 (cyclopropyl) | M.P. 133–134° C. |

In the practical usage of the triazolinones (I) they may be applied as such or in any preparation form such as wettable powders, emulsifiable concentrates, flowables, granules, fine granules or dusts.

For production of said preparation forms, solid or liquid carriers or diluents may be used. As for the solid carrier or diluent, there may be exemplified mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like. As for the liquid carrier or diluent, there may be exemplified alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric ones. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. If necessary, gelatin, casein, sodium alginate, starch, agar, polyvinyl alcohol or the like may be used as an auxiliary agent.

In the herbicidal composition of this invention, the content of the triazolinones (I) may be usually from 1 to 95% by weight, preferably from 5 to 80% by weight.

Practical embodiments of the herbicidal composition according to the invention are illustratively shown in the following examples wherein part(s) and % are by weight.

Formulation Example 1

Eighty parts of Compound No. 1, 2.5 parts of alkylsulfate, 2.5 parts of ligninsulfonate and 15 parts of white carbon are well mixed while being powdered to obtain a wettable powder.

Formulation Example 2

Thirty parts of Compound No. 2, 10 parts of an emulsifier ("Sorpol SM100P" manufactured by Toho Chemical Co., Ltd.) and 60 parts of xylene are well mixed to obtain an emulsifiable concentrate.

Formulation Example 3

Five parts of Compound No. 4, 1 part of white carbon, 5 parts of ligninsulfonate and 89 parts of clay are well mixed while being powdered. The mixture is then well kneaded with water, granulated and dried to obtain a granule.

Formulation Example 4

Five parts of Compound No. 5, 1 part of isopropylphosphate, 64 parts of clay and 30 parts of talc are well mixed while being powdered to obtain a dust.

The triazolinones (I) may be used together with other herbicides to improve their herbicidal activity, and in some cases, to produce a synergistic effect. As the other herbicides, there may be employed phenoxy series herbicides such as 2,4-dichlorophenoxyacetic acid, 2-methyl-4-chlorophenoxyacetic acid (including esters and salts thereof); diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-methoxy-4'-nitrophenyl ether, 2,4-dichlorophenyl-4'-nitro-3'-methoxyphenyl ether and 2,4-dichlorophenyl-3'-methoxycarbonyl-4'-nitrophenyl ether; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,6-triazine and 4-amino-6-tert-butyl-3-methylthio-1,2,4-triazine; urea series herbicides such as 3-(3,4-dichlorophenyl)-1,1-dimethylurea, 3-(3,4-dichlorophenyl)-1-methoxy-1-methylurea, 1-(2,2-dimethylbenzyl)-3-p-tolylurea and 1,1-dimethyl-3-(3-trifluoromethylphenyl)urea; carbamate series herbicides such as isopropyl-N-(3-chlorophenyl)-carbamate and methyl-N-(3,4-dichlorophenyl)carbamate; thiolcarbamate series herbicides such as S-(4-chlorobenzyl)-N,N-diethylthiolcarbamate, S-ethyl-N,N-hexamethylenethiolcarbamate, S-ethyl-N,N-diisobutylthiolcarbamate, S-ethyl-N,N-di-n-propylthiolcarbamate and S-n-propyl-N,N-di-n-propylthiolcarbamate; acid anilide series herbicides such as 3,4-dichloropropionanilide, N-methoxymethyl-2,6-diethyl-α-chloroacetanilide, 2-chloro-2',6'-diethyl-N-butoxymethylacetanilide, 2-chloro-2',6'-diethyl-N-(n-propoxyethyl)acetanilide N-chloroacetyl-N-(2,6-diethylphenyl)glycinethyl ester and 2-chloro-N-(2-ethyl-6-methylphenyl)-N-(2-ethoxy-1-methyl)acetamide; uracil series herbicides such as 5-bromo-3-sec-butyl-6-methyluracil and 3-cyclohexyl-5,6-trimethyleneuracil; pyridinium salt series herbicides such as 1,1'-dimethyl-4,4'-bispyridinium dichloride; phosphorus series herbicides such as N,N-bis(phosphonomethyl)glycine, O-ethyl-O-(2-nitro-5-methylphenyl)-N-sec-butylphosphoroamidothioate and S-(2-methyl-1-piperidylcarbonylmethyl)-O,O-di-n-propyldithiophosphate; toluidine series herbicide such as α,α,α-trifluoro-2,6-dinitro-N,N-dipropyl-p-toluidine; N$^3$,N$^3$-diethyl-2,4-dinitro-6-trifluoromethyl-m-phenylenediamine; 5-t-butyl-3-(2,4-dichloro-5-isopropoxyphenyl)-1,3,4-oxadiazolin-2-one; 3-isopropyl-1H-2,1,3-benzothiadiazin-(4)-3H-one-2,2-dioxide, α-(β-naphthoxy)propionanilide; 4-(2,4-dichlorobenzoyl)-1,3-dimethylpyrazol-5-yl-p-toluenesulfonate; 4'-phenylsulfonyl-1,1,1-trifluorosulfono-O-toluidide; 4-chloro-5-methylamino-2-(3-trifluoromethylphenyl)pyridazin-3(2H)-one; 1-methyl-3-phenyl-5-(3-trifluoromethylphenyl)pyridazin-4(1H)-one; 2-methyl-4-phenylsulfonyl trifluoromethylsulfoanilide; 2-(3,4-dichlorophenyl)-4-methyltetrahydro-1,2,4-oxadiazol-3,5-dione; 4-chloro-5-methylamino-2-(3-trifluoromethylphenyl)pyridazin-3(2H)-one; sodium methanearzonate; etc. But, the herbicides are not limited to these examples.

The herbicides of the invention may be applied together with other insecticides, nematocides, fungicides, plant growth regulators, fertilizers, etc.

The dosage of the triazolinones (I) depends upon their preparation modes, the sorts of cultivated plants or weeds, soil conditions, etc. Generally, however, the dosage of from 1 to 200, preferably from 2.5 to 50, grams of the active ingredient per are is sufficient to control weeds.

The application of the triazolinones (I) as herbicides will be illustratively shown in the following Examples wherein the phytotoxicity to cultivated plants and the herbicidal activity on weeds were evaluated as follows: the aerial parts of the test plants were cut off and weighed (fresh weight); the percentage of the fresh weight of the treated plant to that of the untreated plant was calculated with the latter fresh weight taken as 100; and the crop damage and the herbicidal activity were evaluated by the standard given in the table below. The rating values of phytotoxicity, 0 and 1, and those of herbicidal effect, 5 and 4, are generally regarded as satisfactory to protect cultivated plants and to control weeds, respectively.

| Rating value | Fresh weight (percentage to untreated plot) | |
| --- | --- | --- |
| | Cultivated plant | Weed |
| 5 | 0–39 | 0 |
| 4 | 40–59 | 1–10 |
| 3 | 60 79 | 11–20 |
| 2 | 80–89 | 21–40 |
| 1 | 90–99 | 41–60 |
| 0 | 100 | 61–100 |

The following control compounds were used in the Examples:

| | Remarks |
| --- | --- |
| Control (a) 3-Chloro-1-benzyl-1,2,4-triazolin-5-one | Kroger et al.: Chem. Ber., 102, 755–766 (1969) |

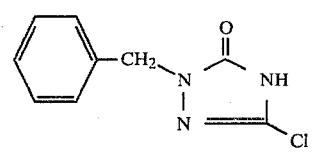

| Control (b) 1,1-Dimethyl-3-(3-trifluoromethylphenyl)urea | Commercially available herbicide known as |

Test Example 1

Plastic pots (10 cm in diameter and 10 cm in height) were filled with upland field soil, and the seeds of barnyardgrass, wild oat, tall morningglory and velvetleaf were sowed therein. The designed amount of the test compound formulated into an emulsifiable concentrate and diluted with water was sprayed to the soil by means of a hand sprayer at a spray volume of 10 liters per are. The test plants were cultivated in a greenhouse and 20 days after the treatment, the herbicidal activity was determined. The results are shown in Table 3.

TABLE 3

| Compound No. | Dosage (weight of active ingredient, g/are) | Herbicidal activity | | | |
|---|---|---|---|---|---|
| | | Barnyard-grass | Wild oat | Tall morning-glory | Velvet-leaf |
| 1 | 80 | 5 | 5 | 5 | 5 |
|   | 40 | 5 | 5 | 5 | 5 |
| 2 | 80 | 5 | 5 | 5 | 5 |
|   | 40 | 5 | 5 | 5 | 5 |
| 3 | 80 | 5 | 5 | 5 | 5 |
|   | 40 | 5 | 5 | 5 | 5 |
| 4 | 80 | 5 | 5 | 5 | 5 |
|   | 40 | 5 | 5 | 5 | 5 |
| 5 | 80 | 5 | 5 | 5 | 5 |
|   | 40 | 5 | 5 | 5 | 5 |
| 6 | 80 | 5 | 5 | 5 | 5 |
|   | 40 | 5 | 5 | 5 | 5 |
| 7 | 80 | 5 | 5 | 5 | 4 |
|   | 40 | 5 | 4 | 4 | 5 |
| 8 | 80 | 5 | 5 | 5 | 5 |
|   | 40 | 5 | 5 | 4 | 5 |
| 9 | 80 | 5 | 5 | 5 | 5 |
|   | 40 | 5 | 5 | 5 | 5 |
| 10 | 80 | 5 | 5 | 5 | 5 |
|    | 40 | 5 | 5 | 5 | 5 |
| 11 | 80 | 5 | 5 | 5 | 5 |
|    | 40 | 5 | 5 | 5 | 5 |
| Control (a) | 80 | 0 | 0 | 0 | 0 |
|    | 40 | 0 | 0 | 0 | 0 |

Remarks: "Cotoran"

Test Example 2

Plastic pots (10 cm in diameter and 10 cm in height) were filled with upland field soil, and the seeds of barnyardgrass, wild oat, wild mustard and velvetleaf were sowed therein and cultivated in a greenhouse for 2 weeks. The designed amount of the test compound formulated into an emulsifiable concentrate was sprayed to the foliage of the test plants over the top by means of a hand sprayer. After the treatment, the test plants were grown for a further 3 weeks in the greenhouse, and the herbicidal activity was determined. The results are shown in Table 4. In this treatment, the emulsifiable concentrate was dispersed in water containing a wetting agent for application at a spray volume of 5 liters per are.

TABLE 4

| Compound No. | Dosage (weight of active ingredient, g/are) | Herbicidal activity | | | |
|---|---|---|---|---|---|
| | | Barnyard-grass | Wild oat | Wild mustard | Velvet-leaf |
| 1 | 40 | 5 | 5 | 5 | 5 |
| 2 | 40 | 5 | 5 | 4 | 5 |
| 3 | 40 | 5 | 5 | 5 | 5 |
| 4 | 40 | 5 | 5 | 4 | 5 |
| 5 | 40 | 5 | 5 | 5 | 5 |
| 6 | 40 | 5 | 5 | 5 | 5 |
| 7 | 40 | 4 | 4 | 4 | 5 |
| 8 | 40 | 5 | 4 | 4 | 5 |
| 9 | 40 | 5 | 5 | 5 | 5 |
| 10 | 40 | 5 | 5 | 5 | 5 |
| 11 | 40 | 5 | 5 | 5 | 5 |
| Control (a) | 40 | 0 | 0 | 1 | 0 |

Test Example 3

Plastic pots (each 500 ml volume) were filled with paddy field soil containing the seeds of various weeds and, water was poured therein until the depth of water became 4 cm. Rice seedlings of a 2 leaved stage and buds of slender spikerush tided over the winter were planted into the pots and grown for 5 days in a greenhouse. The designed amount of the test compound each formulated into an emulsifiable concentrate was applied to the pots by perfusion. Three weeks after the treatment, the herbicidal activity and phytotoxicity were determined on the rice plants as well as the weeds such as barnyardgrass, slender spikerush, broadleaved weeds (e.g. monochoria, false pimpernel, toothcup) and bulrush which were spontaneously germinated in the pots. The results are shown in Table 5. In this treatment, the emulsifiable concentrate was dispersed in water for application at a perfusion volume of 10 liters per are.

TABLE 5

| Compound No. | Dosage (weight of active ingredient, g/are) | Herbicidal activity | | | | Phytotoxicity Rice plant |
|---|---|---|---|---|---|---|
| | | Barn-yard-grass | Broad-leaved weed | Slender spikerush | Bulrush | |
| 1 | 40 | 5 | 5 | 5 | 5 | 0 |
| 2 | 40 | 5 | 5 | 5 | 5 | 1 |
| 3 | 40 | 5 | 5 | 5 | 5 | 0 |
| 4 | 40 | 5 | 5 | 5 | 5 | 1 |
| 5 | 40 | 5 | 5 | 5 | 5 | 2 |
| 6 | 40 | 5 | 5 | 5 | 5 | 1 |
| 7 | 40 | 5 | 5 | 5 | 5 | 0 |
| 8 | 40 | 5 | 5 | 5 | 5 | 0 |
| 9 | 40 | 5 | 5 | 5 | 5 | 1 |
| 10 | 40 | 5 | 5 | 5 | 5 | 1 |
| 11 | 40 | 5 | 5 | 5 | 5 | 1 |
| Control (a) | 40 | 0 | 1 | 0 | 0 | 0 |

Test Example 4

Plastic trays (35 cm × 25 cm × 10 cm) were filled with upland field soil, and the seeds of tall morningglory, velvetleaf, prickly sida, jimsonweed, black nightshade, redroot pigweed, Johnsongrass and green foxtail and the seeds of cotton, soybean and corn were sowed in the trays. The designed amount of the test compound formulated in a wettable powder and dispersed in water was sprayed to the soil by a hand sprayer at a spray volume of 5 liters per are. The test plants were cultivated in a greenhouse. Twenty days thereafter, the herbicidal activity and phytotoxicity were determined. The results are shown in Table 6.

TABLE 6

| Compound No. | Dosage (weight of active ingredient, g/are) | Herbicidal activity | | | | | | | | Phytotoxicity | | |
|---|---|---|---|---|---|---|---|---|---|---|---|---|
| | | Tall morning-glory | Velvet-leaf | Prickly sida | Jimson-weed | Black night-shade | Redroot pigweed | Johnson-grass | Green fox-tail | Cotton | Soybean | Corn |
| 2 | 40 | 4 | 5 | 5 | 5 | 5 | 5 | 5 | 5 | 2 | 2 | 2 |
|   | 20 | 3 | 5 | 5 | 5 | 5 | 5 | 5 | 5 | 1 | 1 | 1 |
| 4 | 40 | 5 | 5 | 5 | 5 | 5 | 5 | 5 | 5 | 0 | 2 | 2 |
|   | 20 | 4 | 5 | 5 | 5 | 5 | 5 | 5 | 5 | 0 | 0 | 0 |
| 5 | 40 | 5 | 5 | 5 | 5 | 5 | 5 | 5 | 5 | 1 | 2 | 2 |
|   | 20 | 5 | 5 | 5 | 5 | 5 | 5 | 5 | 5 | 0 | 1 | 1 |
| Control (b) | 40 | 4 | 4 | 4 | 5 | 5 | 5 | 4 | 4 | 1 | 4 | 3 |
|   | 20 | 3 | 3 | 3 | 3 | 5 | 5 | 2 | 4 | 0 | 2 | 2 |

What is claimed is:

1. A compound of the formula:

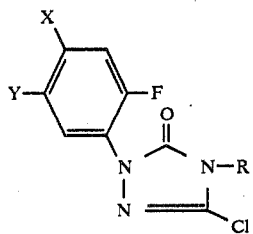

wherein R is a $C_1$-$C_4$ alkyl group, a $C_3$-$C_4$ alkenyl group or a $C_3$-$C_4$ cycloalkyl group, X is a chlorine atom or a bromine atom and Y is a hydrogen atom or a $C_1$-$C_4$ alkoxy group.

2. The compound according to claim 1, wherein R is a $C_1$-$C_4$ alkyl group, a cyclopropyl group or an allyl group and Y is a hydrogen atom or a $C_1$-$C_3$ alkoxy group.

3. 3-Chloro-4-isopropyl-1-(4-chloro-2-fluorophenyl)-1,2,4-triazolin-5-one.

4. 3-Chloro-4-cyclopropyl-1-(4-chloro-2-fluorophenyl)-1,2,4-triazolin-5-one.

5. 3-Chloro-4-cyclopropyl-1-(4-chloro-2-fluoro-5-isopropoxyphenyl)-1,2,4-triazolin-5-one.

6. A herbicidal composition which comprises as an active ingredient a herbicidally effective amount of the compound according to claim 1 and an inert carrier or diluent.

7. A method for controlling weeds which comprises applying a herbicidally effective amount of the compound according to claim 1 to the locus where the control of undesired weeds is encouraged.

8. A compound of the formula:

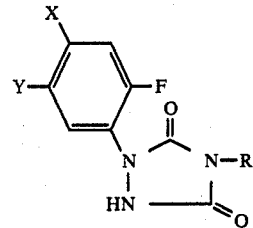

wherein R is a $C_1$-$C_4$ alkyl group, a $C_3$-$C_4$ alkenyl group or a $C_3$-$C_4$ cycloalkyl group, X is a chlorine atom or a bromine atom and Y is a hydrogen atom or a $C_1$-$C_4$ alkoxy group.

* * * * *